(12) United States Patent
Evans et al.

(10) Patent No.: US 12,605,124 B2
(45) Date of Patent: Apr. 21, 2026

(54) X-RAY IMAGING APPARATUS

(71) Applicant: ADAPTIX LTD, Begbroke (GB)

(72) Inventors: Mark Evans, Witney (GB); Stephen Wells, Begbroke (GB)

(73) Assignee: ADAPTIX LTD, Begbroke (GB)

( * ) Notice: Subject to any disclaimer, the term of this patent is extended or adjusted under 35 U.S.C. 154(b) by 280 days.

(21) Appl. No.: 18/383,544

(22) Filed: Oct. 25, 2023

(65) Prior Publication Data

US 2024/0050046 A1 Feb. 15, 2024

Related U.S. Application Data

(63) Continuation of application No. PCT/IB2022/051687, filed on Feb. 25, 2022.

(30) Foreign Application Priority Data

| Mar. 3, 2021 | (GB) | ...................................... | 2103021 |
| Mar. 4, 2021 | (GB) | ...................................... | 2103067 |

(51) Int. Cl.
| *A61B 6/00* | (2024.01) |
| *A61B 6/02* | (2006.01) |
| *A61B 6/04* | (2006.01) |
| *A61B 6/40* | (2024.01) |

(52) U.S. Cl.
CPC ............ *A61B 6/025* (2013.01); *A61B 6/0407* (2013.01); *A61B 6/4085* (2013.01); *A61B 6/4441* (2013.01)

(58) Field of Classification Search
CPC ............................ A61B 6/025; H01J 2235/068
See application file for complete search history.

(56) References Cited

U.S. PATENT DOCUMENTS

| 8,488,737 B2 * | 7/2013 | Boese | .................. A61B 6/4021 |
| | | | 378/62 |
| 2010/0329416 A1 | 12/2010 | Tsujii | |
| 2012/0008739 A1 | 1/2012 | Hoernig et al. | |
| 2014/0153690 A1 | 6/2014 | Claus et al. | |

(Continued)

FOREIGN PATENT DOCUMENTS

| DE | 102010028438 | 11/2011 |
| DE | 102010039080 | 2/2012 |

(Continued)

OTHER PUBLICATIONS

UKIPO, Search Report in corresponding GB application GB2103067.1, Mar. 3, 2023.

(Continued)

*Primary Examiner* — Dani Fox
(74) *Attorney, Agent, or Firm* — Alley IP

(57) ABSTRACT

An x-ray imaging apparatus 10 comprising a support 30 having two arms, wherein on one arm an x-ray emitter 50 is arranged, and on the other arm a flat panel digital detector 60 is arranged, the emitter and detector arranged opposite each other providing a space therebetween for the positioning of an object for x-ray imaging by the apparatus, the x-ray emitter comprising an array of emitters, the apparatus arranged such that in use different emitters are energisable independently from one another such that 3-dimensional tomosynthesis images are obtainable of the object, with the object, emitter and detector maintained stationary relative to one another.

8 Claims, 6 Drawing Sheets

(56)           References Cited

U.S. PATENT DOCUMENTS

| | | | | |
|---|---|---|---|---|
| 2015/0049862 A1* | 2/2015 | Ancar | ................... | A61B 6/588 |
| | | | | 378/190 |
| 2015/0216493 A1* | 8/2015 | Kim | .................... | A61B 6/0407 |
| | | | | 378/198 |
| 2015/0223767 A1* | 8/2015 | Sehnert | .................. | A61B 6/547 |
| | | | | 378/42 |
| 2019/0029611 A1* | 1/2019 | Travish | .................. | A61B 6/102 |
| 2020/0182807 A1* | 6/2020 | Butani | ............. | G01N 23/20025 |

FOREIGN PATENT DOCUMENTS

| | | |
|---|---|---|
| EP | 3064140 | 9/2016 |
| GB | 2588385 | 4/2021 |
| WO | 2017/130013 | 8/2017 |
| WO | 2017/173341 | 10/2017 |
| WO | 2020/117734 | 6/2020 |

OTHER PUBLICATIONS

WIPO, International Search Report in corresponding PCT application PCT/IB2022/051687, Jun. 3, 2022.

WIPO, Written Opinion in corresponding PCT application PCT/IB2022/051687, Jun. 3, 2022.

Travish et al., "Applying high frame-rate digital radiography and dual-energy distributed-sources for advanced tomosynthesis" Proc. SPIE 8853, Medical Applications of Radiation Detectors III, 88530H, Sep. 26, 2013.

Travish et al., "Addressable flat-panel x-ray sources for medical, security, and industrial applications" Proc. of SPIE vol. 8502, 85020L, Dec. 21, 2012.

* cited by examiner

450

451    Anode, enthaltend
Target, Durchführung
und Pinch-Off-Rohr

452    Schutzring

453    Emitter-Array

454    Kathode

X-RAY IMAGING APPARATUS

RELATED APPLICATIONS

This application claims the benefit under 35 U.S.C. § 120, and is a continuation, of co-pending International Application PCT/IB2022/051687, filed Feb. 25, 2022 and designating the US, which claims priority to GB Application 2103021.8, filed Mar. 3, 2021 and GB Application 2103067.1, filed Mar. 4, 2021, such GB Applications also being claimed priority to under 35 U.S.C. § 119. These GB and International applications are incorporated by reference herein in their entireties.

BACKGROUND

Field

The present invention relates generally to an x-ray imaging apparatus in the form of a "C" shape device and finds particular, although not exclusive, utility in medical x-ray imaging.

SUMMARY

In a first aspect, the invention provides an x-ray imaging apparatus comprising two arms, wherein on one arm an x-ray emitter is arranged, and on the other arm a flat panel digital detector is arranged, the emitter and detector arranged opposite each other providing a space therebetween for the positioning of an object for x-ray imaging by the apparatus, the x-ray emitter comprising an array of emitters, the apparatus arranged such that in use different emitters are energisable independently from one another such that 3-dimensional tomosynthesis images are obtainable of the object, with the object, emitter and detector maintained stationary relative to one another.

The x-ray imaging apparatus may include a control box, wherein the combination of the apparatus and control box may have an outer size less than 50×50×50 cm (height by width by depth).

The mass of the combination of the apparatus and control box may be no more than 25 kg.

The x-ray imaging apparatus may comprise a high voltage generator within the x-ray emitter for producing beams of electrons.

The x-ray imaging apparatus may comprise solenoids for directing the beams of electrons onto either x-ray producing material or onto electron absorbing material so as to control the production of x-rays from selected emitters in the array. The term "electron absorbing material" may mean that the material produces substantially no, or only few, x-rays.

The x-ray emitter may comprise a vacuum enclosure which includes a circular cathode and a circular anode separated by an annular spacer.

The detector may have pixels less than or equal to 100 μm in width.

The x-ray emitter may comprise an internal collimator, a yoke, and a secondary collimator for restricting the cone angle of the emitted x-rays. In this respect, the cone angle may be 38 degrees, (i.e. a half angle cone of 19 degrees).

The x-ray imaging apparatus may further comprise a support and a pivot for enabling rotation of the two arms relative to the support.

The x-ray imaging apparatus may further comprise means for raising and lowering the two arms relative to the support.

The apparatus comprises two arms such that the overall shape is a Roman alphabet "C" or "U" with two arms. The apparatus is attachable to a support in between the two arms. The apparatus may be rotatable about the attachment point and thus the attachment point may comprise a pivot. The apparatus may enable imaging in at least two positions; with the source vertically above the detector (primarily for hand and wrist imaging); or, with the source and detector horizontal to each other (primarily for mass-bearing foot and ankle imaging). Angles in between these two are also possible.

The attachment may allow for the quick removal of the apparatus from one mounting to another such that the apparatus may be mounted on a desk mount, or a trolley mount, for instance. A motor may be provided to raise or lower the apparatus relative to its mounting. When on the trolley, the mounting may allow the apparatus to be positioned such that the detector surface is more than or equal to 100 cm above the floor; such that the detector surface is less than or equal to 10 cm above the floor; such that the side detector active area is <15 cm above the floor.

When on the desk mount, the mounting may allow the apparatus to be positioned such that the detector surface is less than or equal to 15 cm above a desk surface; such that the edge of the detector active area is less than or equal to 15 cm above the floor.

Towards, or at, the end of one arm the x-ray source is arranged. Towards, or at, the end of the other arm the x-ray detector is arranged. In use, the apparatus may provide 3D tomosynthesis images of a subject.

The apparatus may have a rigid frame, holding the x-ray source from the detector with a fixed SID of approximately 200 mm. In one example, the apparatus may have a fixed Source to Image Distance (SID) that is more than 19.5 cm and less than 20.5 cm (distance between the X-ray source focal spot and the detector). The apparatus may include a frame comprising aluminium tubing.

The detector size may have pixels less than or equal to 100 lam wide and an area of at least 14×11 cm. A control box may be provided which may include a power supply unit and a CPU. The control box size may be less than 40×30×20 cm. The apparatus may weigh less than 16 kg. By contrast, the control box may weigh less than 10 kg. The x-ray source may provide a tomosynthesis angular range of at least 15° in the centre of the detector. The angular range for tomosynthesis at the edge of the detector may be more than 80% of that at the centre.

The apparatus may operate from a 13 A, 110V to 240V mains electricity supply. The apparatus may operate at a fixed voltage within 5% of 60 kV. The apparatus may emit X-rays from at least 30 different positions. The focal spot diameter for each emitter may be less than or equal to 1 mm. The x-ray generator (within the x-ray source) may provide filtration equivalent to applying 1.5 mm of Al filtration to an RQR 4 source.

It may be possible for a single user to change between horizontal and vertical positioning of the apparatus within 1 minute.

The x-ray source may be known as an "FPS"—flat panel source. The FPS may include a set of hardware and software components which may provide a controllable array of X-ray sources, an integrated high voltage supply, control electronics and firmware, external control software for the device, essential calibration systems, and software to convert X-ray images collected with the device into usable images for a medical practitioner.

The FPS may include an X-ray generator which is a controllable array of X-ray sources. In use, the X-rays may pass through part of the patient and form an image on the detector. The detector may be responsive to X-rays of the energy produced by the source, and may have an appropriate spatial resolution for the detail which is expected. The detector may be capable of collecting a series of images in quick succession. A rapid dynamic detector may require precisely timed control and the ability to offload the collected data at an appropriate rate.

The X-ray generator and detector are held in more or less precise alignment by the arms. These serve a number of purposes, including supporting the mass of the components, providing positioning to achieve alignment and a particular source-image distance, and providing separation between the X-ray source and the surface (skin) of the patient.

A low voltage power supply may be provided for powering the X-ray generator, its electronics, to operate the controls for the individual X-ray sources (such as solenoids for diverting beams of electrons between x-ray producing targets and electron absorbing material), and to power an integrated source of high voltages to operate the x-ray sources (to produce the electrons).

In use, the X-ray generator may produce a number of X-ray pulses, of known intensity and duration, from known positions, in a defined sequence. After detection by the detector a set of images representing slices through the imaged object may be produced by the CPU.

Within the X-ray generator, high voltages may be used to (a) generate free electrons from the emitters and (b) accelerate those electrons so they produce X-rays when they hit a suitable target. Accelerating the electrons requires energy and the power required is proportional to both the current of the electron beam and the accelerating voltage.

A high voltage generator may be provided that produces the required voltage and current. This HV generator may maintain a potential of up to 60 kV while supplying up to 2.5 mA of current. This is a maximum power output of 150 W. The current sourced by the HV generator is equal to the current of the electron beam. The potential is supplied by keeping an electrode at −60 kV relative to ground (0 V).

To avoid possible harms and loss of functionality, the HV generator may include an epoxy encapsulation layer (potting) that completely encloses it. The potting may extend over the surface of the x-ray source monolith from the cathode to the top of the ceramic spacer, providing the same high voltage protection to that subassembly. The potting may thus prevent high voltage breakdown within the HV generator and on the external surface of the monolith, and prevent harmful external exposure to the high voltages generated within the HV generator and present on the adjacent surface of the monolith.

A control board may provide the power and control inputs needed by the HV generator, and may monitor and report its output, and may ensure that it can only operate for a limited time.

The X-ray source (monolith) may convert electrical energy provided by the HV generator into X-rays. It may be an ultra-high vacuum enclosure that contains a field emitter array and a target/collimator subassembly. The vacuum enclosure may be constructed from a circular cathode and a circular anode separated by an annular spacer. The cathode may be connected to the high voltage (−60 kV) output generated by the HV generator. The anode may be shaped to allow the emission of X-rays and to position the control coils from the coils and yoke subassembly.

Within the monolith, the field emitter array may generate a number of streams of electrons and the target/collimator subassembly either re-absorbs these electrons or generates X-rays in a way that gives the effect of turning the emitters on or off. The alignment of the target/collimator subassembly with the rest of the monolith is such that x-ray emission is prevented when no control coils are active, because the electron beams from the emitter array strike the collimator. When an emitter is "switched on", its electron beam will strike a target layer and the resulting X-rays will pass through a hole in a collimator layer and exit the monolith.

Each individual emitter is turned on or off through control coils that generate magnetic fields which are used to steer the electron beam towards an "on" position which is centered at the bottom of a well in the anode.

The subsystem may be designed such that the coils and collimator fit very closely to the anode of the monolith with the required level of alignment specified in the hardware requirements When the X-rays are generated, they may emerge from the point where they are generated in all directions and in straight lines. By tracing back all the rays, one can identify a region within which all these generation points lie. This defines a focal spot for each emitter.

In order to give a predictable and uniform field of X-rays as the basis of imaging and reconstruction, various collimating elements may be used to define a cone, with its vertex at the emitter focal spot. This cone may intersect with the detector to form a circular, or more realistically an elliptical, image, whose edge shape and intensity distribution can be predicted. Collimating elements close to the focal spot may, when well aligned, be most effective at absorbing the unwanted emission. More distant elements may produce more sharply defined features at the edges of the final images.

The internal collimator, yoke, and secondary collimator may be used to restrict the cone angle. The final angle may be 38 degrees (that is, a 19 degrees half angle). Elements closer to the focal spot may use a larger cone angle, so that a predictable final image can be formed without requiring excessively precise alignment of elements at different distances from the focal spot.

The coils may be physically mounted onto the yoke and the control board. They may be outside the vacuum enclosure, but their effect must be felt by electrons below the internal collimator. For this reason, they may be inset in wells in the anode.

The apparatus may have a size less than 50×50×50 cm. The X-ray detector may have pixels less than or equal to 100 lam wide and an area of at least 14×11 cm.

The apparatus may have a mode in which it can perform a scout image i.e. a low dose 2D image covering enough of the subject so the radiographer can confirm that the field of view is correct and so that a calculation can be made to determine the output that would be needed for a good quality tomosynthesis image of the subject.

The apparatus may be configured to vary the overall output (in mAs) to suit subjects of different thickness. It may be possible to reconstruct planes with pixels of 100×100 lam or less in the x-y plane and a spacing between planes of one mm or less in the z direction. It may be possible to configure the spacing between reconstructed 2D planes within set limits. The reconstruction process may be tolerant of normal human motion which could reasonably be expected when a patient attempts to stay still during the acquisition. A reconstruction module may be provided which may produce a set of 2D reconstructed planes in DICOM DX format including basic meta-data about the acquisition.

The apparatus may include a default viewing solution for the DICOM images which are generated.

The apparatus may be able to image patients covering up to the 95% percentile of human body sizes.

The x-ray source may be able to start an x-ray emission less than three seconds from when the request is received by the source. The first reconstructed image plane may be available to view after less than fifteen seconds. A complete dataset of at least fifty planes should be available to view after less than two mins.

The X-ray generator may be able to perform six acquisitions during thirty minutes with at least a one minute gap between acquisitions. The HV generator may be completely enclosed with the X-ray source.

The apparatus may be arranged to limit maximum X-ray output to less than 70 kV and less than 200 µA so that exposure rate is still relatively low even if an accidental exposure did occur. The apparatus may have a sturdy base that will not topple if tilted by 15°.

The apparatus mass may not exceed 25 kg.

Any point on the area in the plane of the detector outside the chosen area of illumination may receive less than 5% of the incident radiation hitting the centre of the illuminated area.

BRIEF DESCRIPTION OF THE DRAWINGS

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

DETAILED DESCRIPTION

Figure 1:
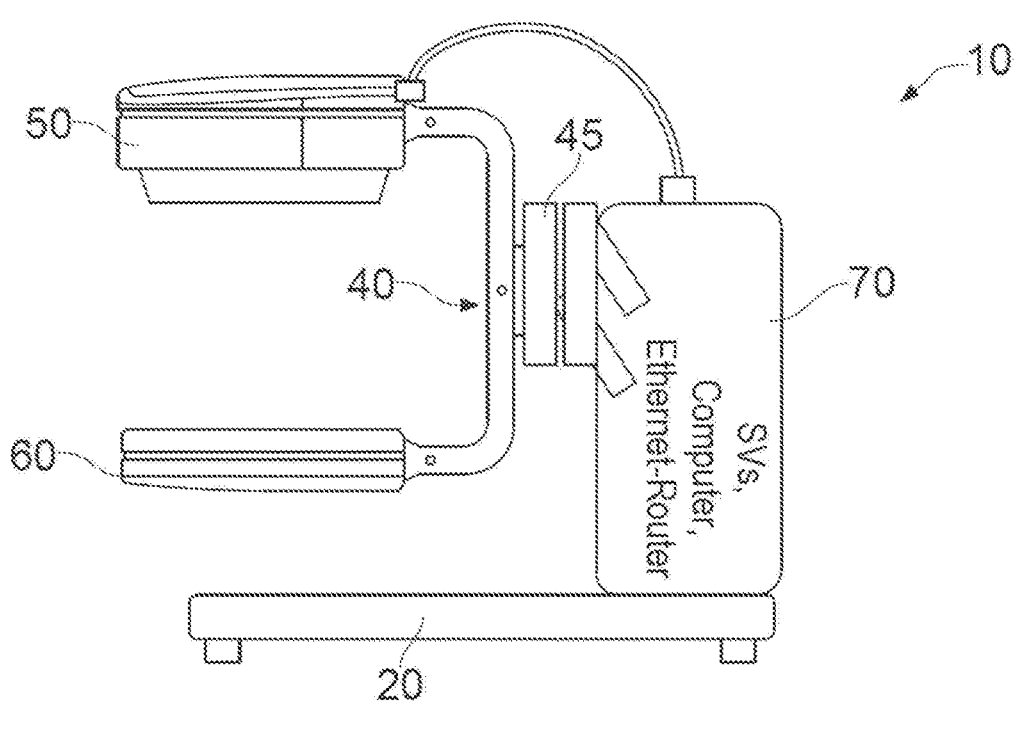
FIGS. 1 to 3 are schematic elevational views of x-ray imaging apparatus.

FIG. 1 shows an example x-ray imaging apparatus 10 comprising a base 20, a control box 70 and a "U" shaped arm 30 supported on the control box 70 by an adjustable arm 45. A pivot 40 arranged between the adjustable arm 45 and the U-shaped arm 30 allows the latter to rotate about a horizontal axis.

On the upper arm an x-ray emitter 50 is arranged. On the lower arm a detector 60 is arranged. The x-ray emitter 50 and detector 60 face each other and are spaced apart such that a subject may be inserted in between for imaging.

The control box 20 includes power supply units, a processor (such as a computer) and communication means such as an ethernet router.

Figure 2:
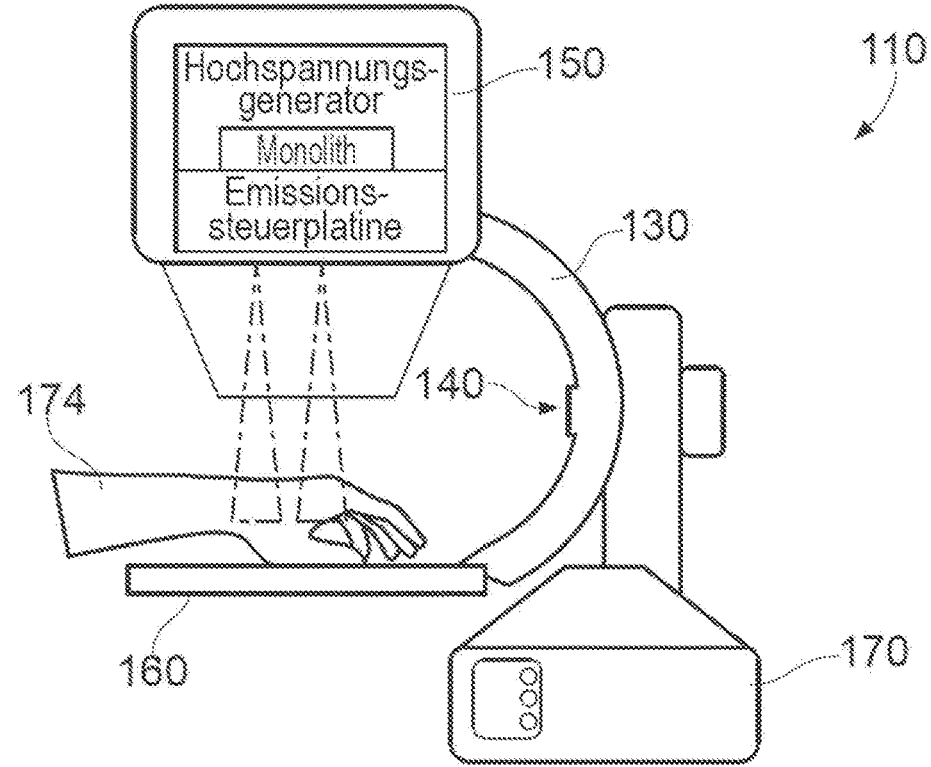

FIG. 2 shows another example x-ray imaging apparatus 110 comprising a base 170, in which the control box is provided and a "U" shaped arm 130 supported on the base 170 by an adjustable arm 180. A pivot 140 arranged between the adjustable arm 180 and the U-shaped arm 330 allows the latter to rotate about a horizontal axis.

On the upper arm an x-ray emitter 150 is arranged comprising a high voltage generator, a monolith and a control board. On the lower arm a detector 160 is arranged. The x-ray emitter 150 and detector 160 face each other and are spaced apart such that a subject may be inserted in between for imaging. A hand 174 is shown in position for imaging thereof.

Figure 3:
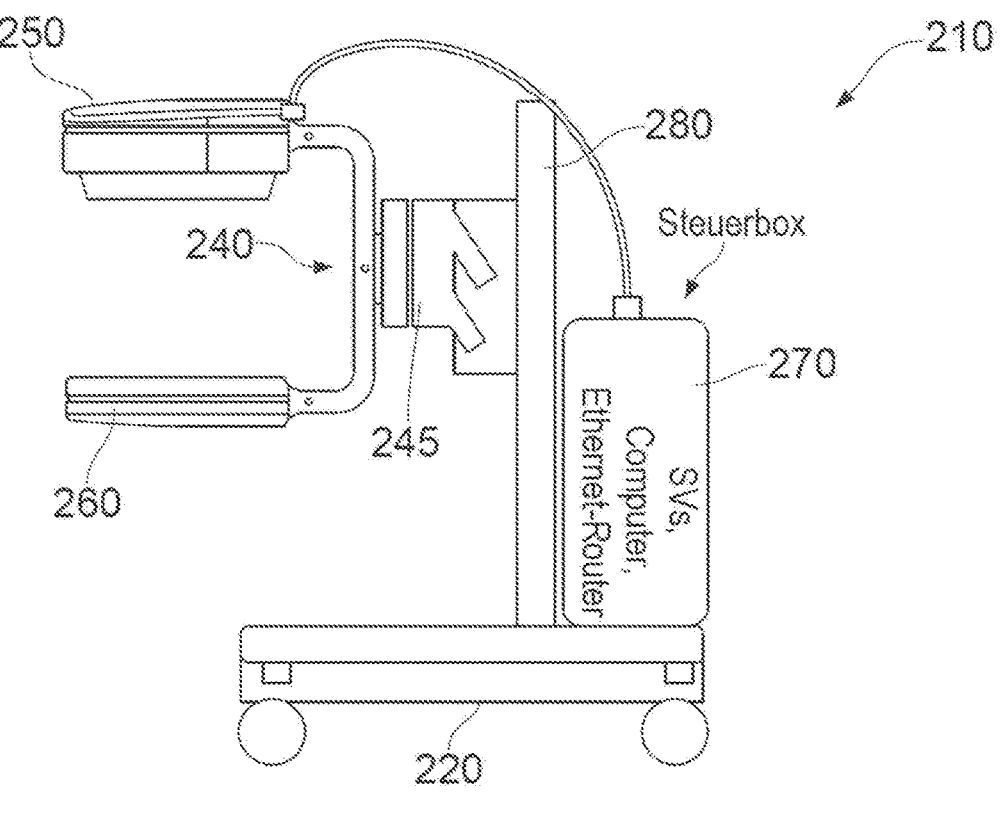

FIG. 3 shows another example x-ray imaging apparatus 210 comprising a base 220 including wheels for movement thereof, a control box 270 on the base, and a "U" shaped arm 230 supported on by an adjustable arm 245 which is itself attached to a support 280 which is vertically mounted on the base 220. A pivot 240 arranged between the adjustable arm 245 and the U-shaped arm 330 allows the latter to rotate about a horizontal axis.

On the upper arm an x-ray emitter 250 is arranged. On the lower arm a detector 260 is arranged. The x-ray emitter 250 and detector 260 face each other and are spaced apart such that a subject may be inserted in between for imaging.

Figure 4:
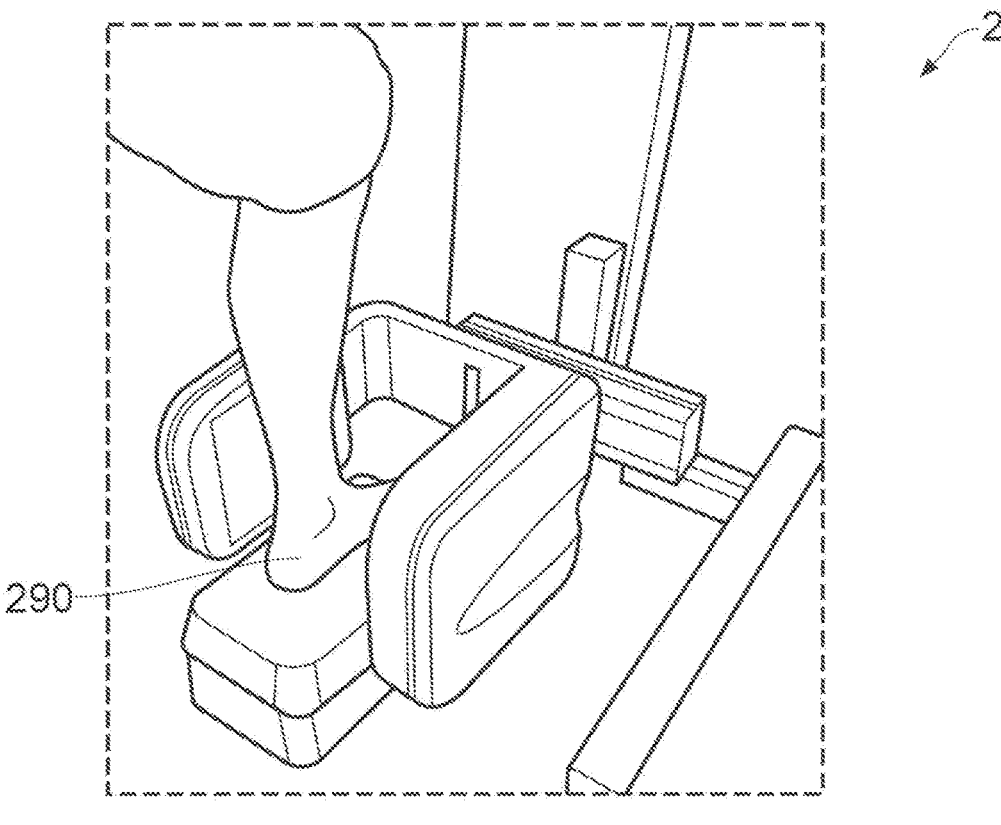
FIGS. 4 to 6 are photographs of x-ray imaging apparatus in use.
Figure 5:
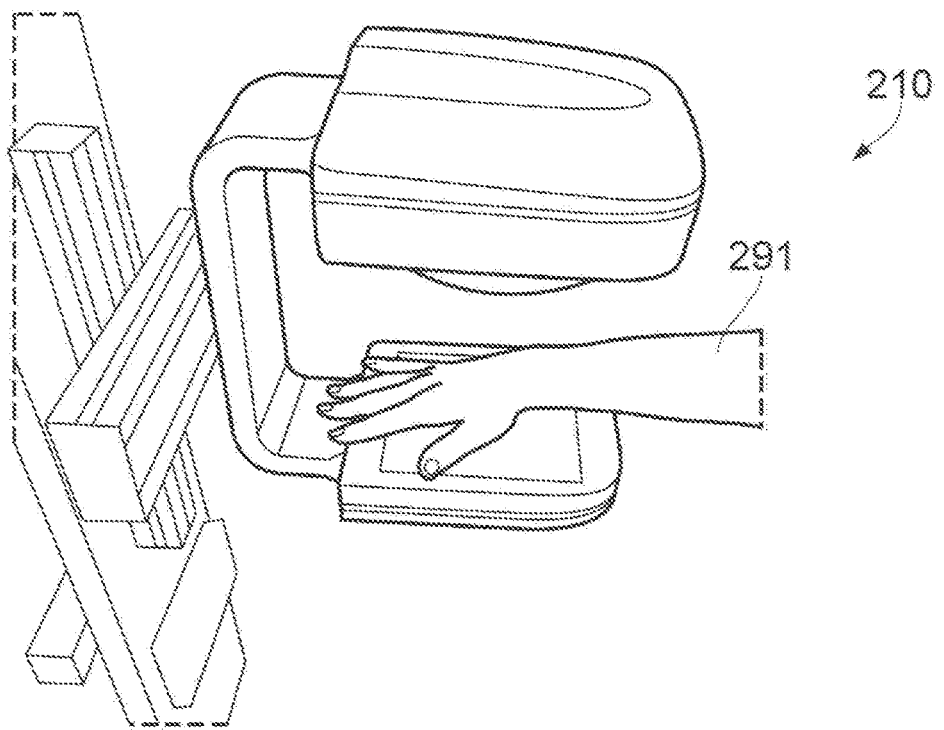
Figure 6:
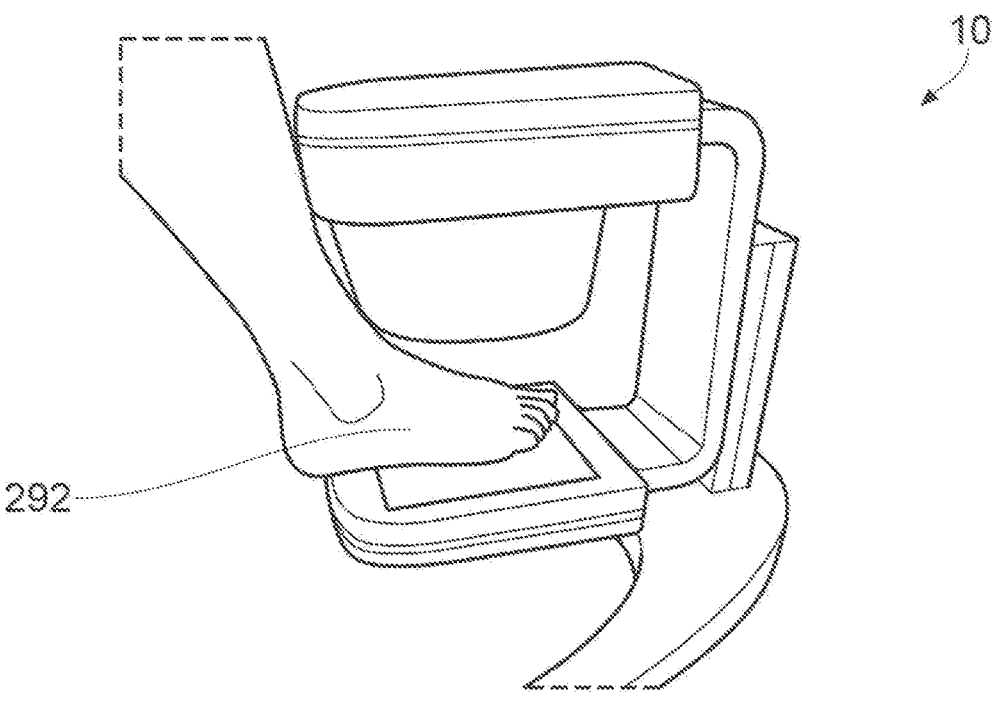

FIGS. 4, 5 and 6 show x-ray imaging apparatus 10, 110 210 of the type shown in FIGS. 1 to 3 being used with a patient to image their ankle 290, hand 291 and foot 292 respectively.

Figure 7:
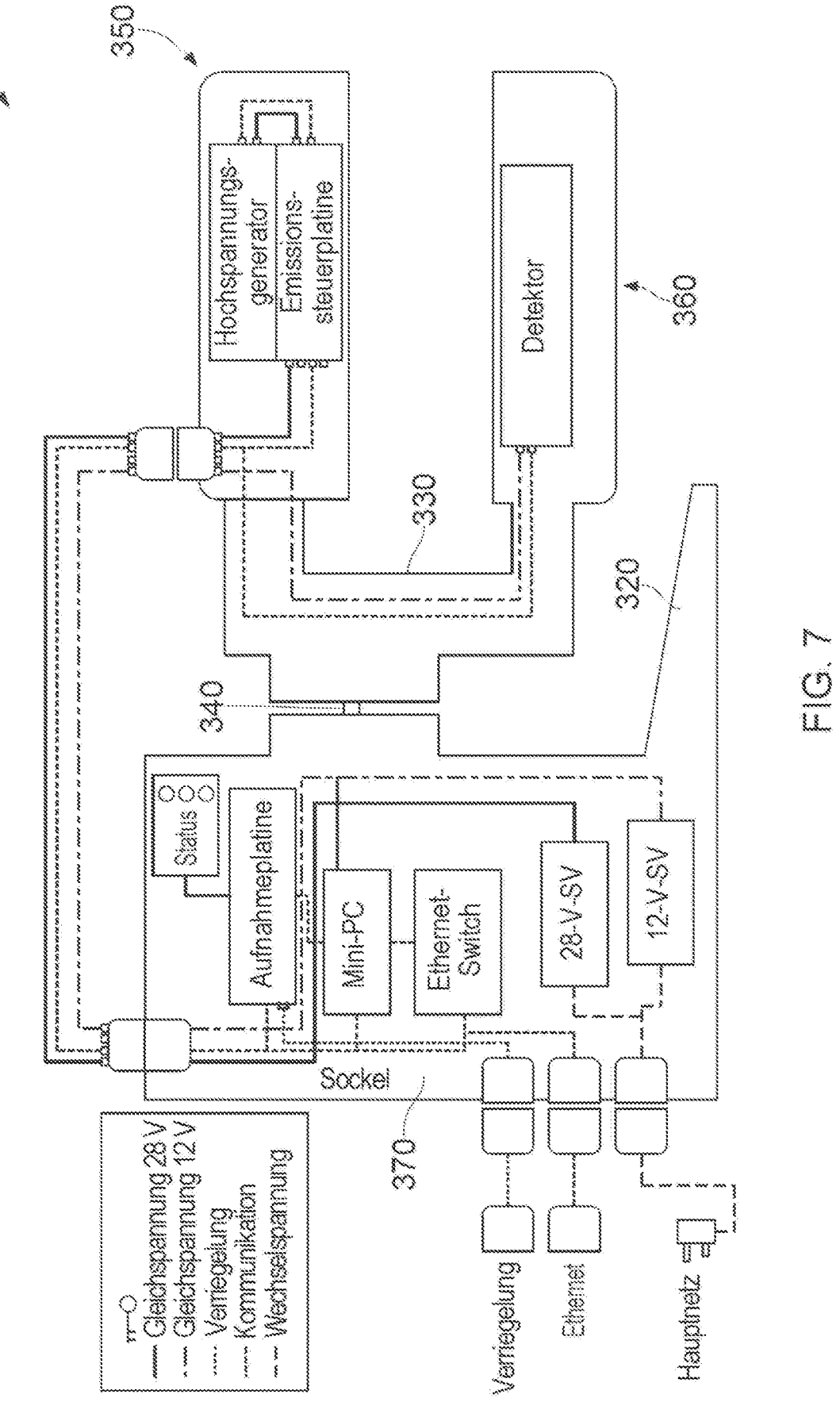
FIG. 7 is a schematic elevational view of components forming an x-ray imaging apparatus.

FIG. 7 shows a schematic side view of an x-ray imaging apparatus 310 including a base 320, a control box 370, a U-shaped arm 330 pivotally connected to the control box by a pivot 340. The upper arm 330 includes an x-ray emitter 350 comprising a high voltage generator and a control board. The lower arm includes a detector 360. The control box 370 comprises a processor, power supplies and other components necessary for the operation of the apparatus.

Figure 8:
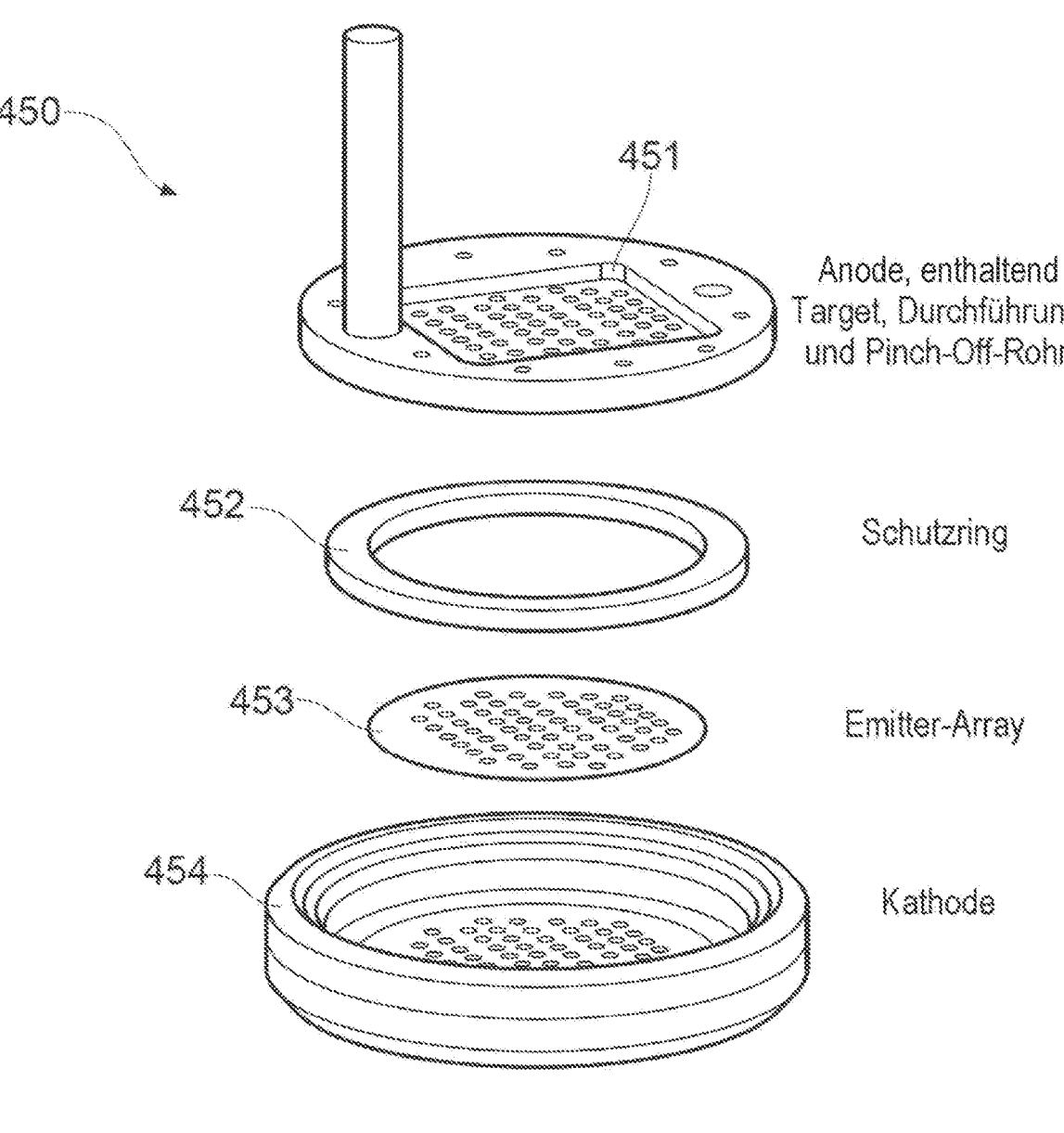
FIG. 8 is an exploded image of part of an x-ray generator.

FIG. 8 shows an exploded view of part of an x-ray emitter 450 comprising an anode 450, a guard ring 452, an emitter array 453 and a cathode 454. The emitter array 453 comprises a two-dimensional array of more than fifty emitters in an organised pattern.

Figure 9:
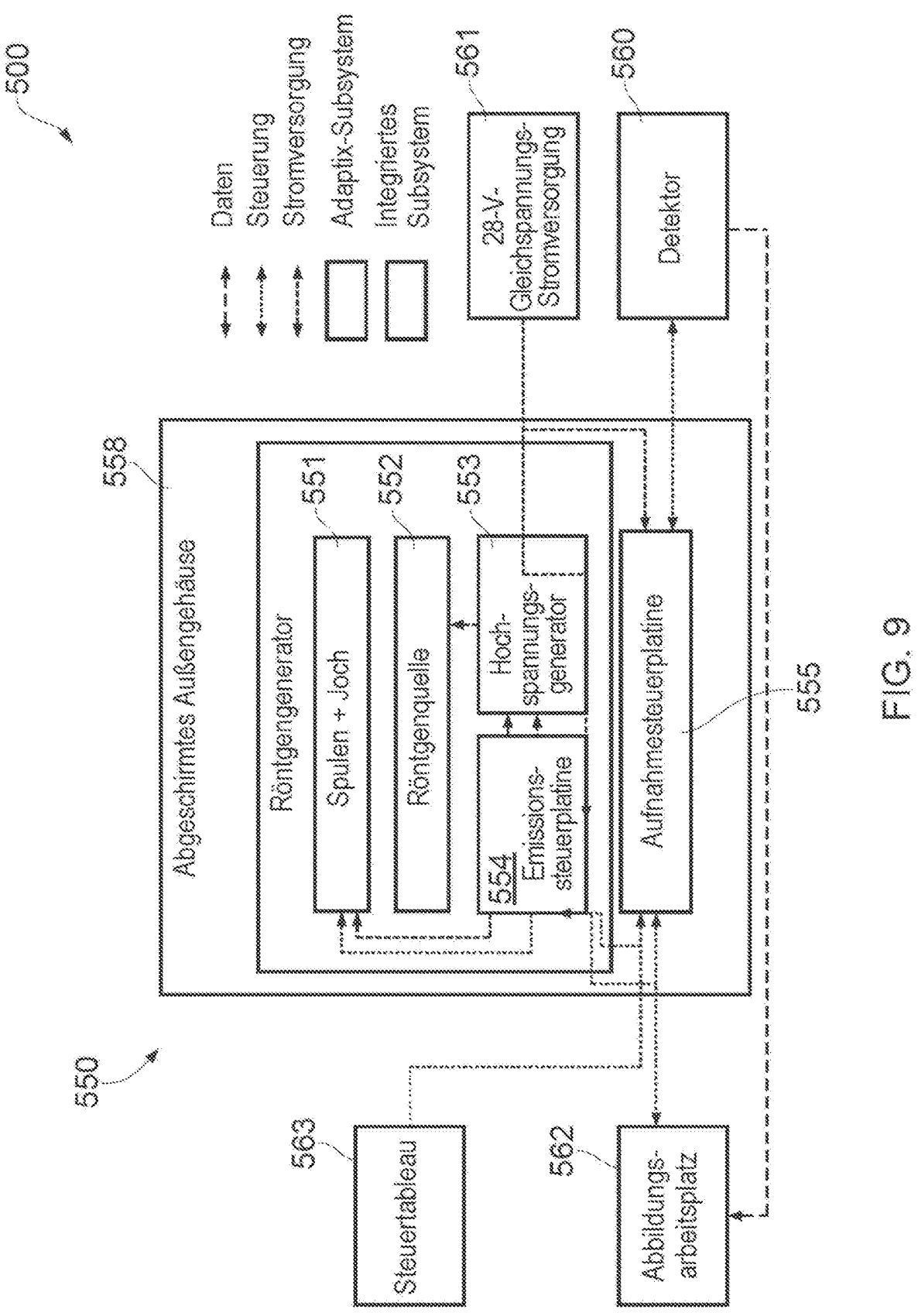
FIG. 9 is a schematic plan of the components of an x-ray imaging apparatus.

FIG. 9 depicts in schematic form 500 the main components necessary to put the apparatus into operation. The emitter 550 is seen to include an outer shielding 558 within which are arranged the 4 coils and yoke 551, the x-ray source 552, the control board 554, and the high voltage generator 553. An acquisition control board 555 controls the emitter in conjunction with the detector 560 to ensure the acquisition of sufficient number of images using different patterns of emitters such that 3D tomosynthesis images are displayable on the imaging work station 562. A control panel 563 provides a user interface. A power supply 561 is also provided.

The invention claimed is:

1. An x-ray imaging apparatus comprising:
   two arms, wherein on one arm an x-ray emitter is arranged, and on the other arm a flat panel digital detector is arranged, the emitter and detector arranged opposite each other providing a space therebetween for the positioning of an object for x-ray imaging by the apparatus, the x-ray emitter including,
   a vacuum enclosure which includes a circular cathode and a circular anode separated by an annular spacer,
   an array of emitters, the apparatus arranged such that in use different emitters are energisable independently from one another such that 3-dimensional tomosynthesis images are obtainable of the object, with the object, emitter, and detector maintained stationary relative to one another, a high voltage generator within the x-ray emitter for producing beams of electrons, and solenoids for directing the beams of electrons onto either x-ray producing material or onto electron absorbing material so as to control the production of x-rays from selected emitters in the array, the solenoids disposed outside of the vacuum enclosure and inset into wells in the anode, wherein the mass of the x-ray imaging apparatus is no more than 25 kg.

2. The x-ray imaging apparatus of claim 1, including a control box, wherein the combination of the apparatus and control box has an outer size less than 50×50×50 cm (height by width by depth).

3. The x-ray imaging apparatus of claim 1, wherein the detector has pixels less than or equal to 100 μm in width.

4. The x-ray imaging apparatus of claim 1, wherein the x-ray emitter comprises an internal collimator, a yoke, and a secondary collimator for restricting the cone angle of the emitted x-rays.

5. The x-ray imaging apparatus of claim 4, wherein the cone angle is 38 degrees.

6. The x-ray imaging apparatus of claim 1, further comprising a support and a pivot for enabling rotation of the two arms relative to the support.

7. The x-ray imaging apparatus of claim 6, further comprising means for raising and lowering the two arms relative to the support.

8. The x-ray imaging apparatus of claim 1, further comprising a Source to Image Distance (SID) of approximately 200 mm.

* * * * *